United States Patent [19]

Rau

[11] Patent Number: 5,110,603
[45] Date of Patent: May 5, 1992

[54] BATHING PREPARATION FOR COLLOIDAL MATERIAL

[75] Inventor: Allen H. Rau, Cincinnati, Ohio

[73] Assignees: Kao Corporation, Tokyo, Japan; The Andrew Jergens Company, Cincinnati, Ohio

[21] Appl. No.: 648,871

[22] Filed: Jan. 31, 1991

[51] Int. Cl.$^5$ ............................................. A61K 9/20
[52] U.S. Cl. ................................ 424/466; 514/957; 424/465
[58] Field of Search ................... 424/44, 464, 466; 514/957

[56] References Cited

U.S. PATENT DOCUMENTS

| | | | |
|---|---|---|---|
| 4,650,667 | 3/1987 | Eguchi | 424/44 |
| 4,678,661 | 7/1987 | Gergely | 424/44 |
| 4,687,662 | 8/1987 | Schobel | 424/44 |
| 4,704,269 | 11/1987 | Korab | 514/957 |
| 4,942,039 | 7/1990 | Duvall | 424/464 |

Primary Examiner—Thurman K. Page
Assistant Examiner—William E. Benston, Jr.
Attorney, Agent, or Firm—Oblon, Spivak, McClelland, Maier & Neustadt

[57] ABSTRACT

A bath preparation comprises a composition which, when dissolved in water, generates carbon dioxide, the composition being physically bound together as a tablet, with a colloidal material. The effervescence produced by dissolving the tablet improves dispersion of the colloidal material, and maintaining said colloidal material in dispersed form in the water for a longer period of time. The colloidal material is selected so as to provide relief from skin irritation. An acid, carbonate salt, and a colloidal material such as colloidal oatmeal may be tableted to provide an effective, easily stored and handled product.

14 Claims, No Drawings

BATHING PREPARATION FOR COLLOIDAL MATERIAL

BACKGROUND OF THE INVENTION

1. Field of the Invention

This invention pertains to a bathing preparation comprising colloidal material in a formulation intended to effervesce in bath water. The effervescence aids in dispersal and delivery of the colloidal particle, as well as providing skin stimulation and fatigue relief in its own right. A method of treating skin irritation with the colloidal material is also addressed.

2. Background of the Prior Art

Bathing preparations which dissolve in warm or hot bath water to effervesce by the release of carbon dioxide as a reaction product in order to stimulate the skin and provide fatigue relief are well known. One example is that disclosed in U.S. Pat. No. 4,666,707, the entirety of which is incorporated herein by reference. In this patent, a moisturizer is incorporated in a carbonate salt/acid combination. When dissolved, the carbonate and acid react to release carbon dioxide. The weakly acidic pH of the resulting water keeps $CO_2$ in solution, prolonging and promoting the effects of $CO_2$ skin stimulation, synergistically enhanced by the moisturizer.

Other effervescing bath preparations are also known. A fundamental preparation is disclosed in U.S. Pat. No. 4,650,667. A further example is disclosed in U.S. patent application Ser. No. 07/324,885, filed Mar. 17, 1989, allowed. This preparation employs low-cost fumaric acid. Preparations of the type described are in commercial use, and available under the trademark ACTIBATH ® as well as other names.

The treatment of minor skin irritations, and in particular, relief from itching induced by inflammation, disease, trauma and the like, through the water-mediated application of colloidal materials is well known. Prominent among various materials of this type is colloidal oatmeal, commercially available under the mark AVEENO ® from S. C. Johnson Company, as well as from other sources. Hydrophobic starches are also well known in this application, as materials which, when dispersed in water, settle on and desensitize the skin, and provide temporary relief.

In general, the colloidal material treatments are effected by dispersing the colloidal material in bath water, and then bathing in the bath suspension. This method presents a number of problems.

Maximum effectiveness is achieved by thorough dispersion of the colloidal material throughout the bath water. As these materials are generally in powder form, not only is this a physically awkward operation, but thorough dispersion tends to be frustrated by the tendency of these materials to swell, soften and agglomerate upon moistening.

Further, agglomerated particles of this type tend to settle relatively rapidly, according to Stokes Law, which provides a particle's settling rate in a dispersing fluid will be governed by its relative diameter and density as well as the fluid's viscosity and density.

Due to the colloidal nature of this material, it tends to persist in the tub or bathing enclosure even after draining of the water. The greater the degree of agglomeration, the more difficult it may be to remove residual material.

It therefore remains an object of those of skill in the art to secure the fatigue relief benefits of $CO_2$ skin stimulation and effervescence, and make the benefits of bathing with colloidal material easier to secure.

SUMMARY OF THE INVENTION

The invention comprises a colloidal material physically bound, such as a tablet form, with a carbonate salt and an acid combination which will effervesce when dissolved in warm or hot bath water. The effervescing activity serves to enhance dispersion of the colloidal material by preventing agglomeration of the material while simultaneously accelerating the particles away from the tablet throughout the bath water. By placing the colloidal material in close proximity to the source of effervescence, the colloidal material may be "auto-dispersed" throughout the bath water, eliminating the need to disperse the material by introducing it into a stream of running water by hand sprinkling, coupled with subsequent stirring of the water. After bathing, the colloidal material having agglomerated to a reduced degree, if at all, the material is easier to drain from the tub or bathing enclosure.

DETAILED DESCRIPTION OF THE INVENTION

The effervescing material of this invention incorporates a carbonate salt and an acid selected to release carbon dioxide when dissolved in warm or hot bath water. Exemplary combinations of this type are set forth in U.S. Pat. No. 4,666,707. The carbonate salt to be used includes sodium hydrogen carbonate, sodium carbonate, sodium sesquicarbonate, potassium hydrogen carbonate, potassium carbonate, potassium sesquicarbonate, ammonium hydrogen carbonate, ammonium carbonate, and ammonium sesquicarbonate. These may be used either alone, or as a mixture of two or more.

These carbonates may be combined with any of a variety of acids, including formic acid, straight-chain aliphatic acids such as acetic acid, propanoic acid butyric acid and valeric acid; dicarboxylic acids such as oxalic acid, malonic acid, succinic acid, glutaric acid, adipic acid, pimelic acid, fumaric acid, maleic acid, phthalic acid, isophthalic acid and terephthalic acid; acidic amino acids such as glutamic acid and aspartic acid; hydroxy acids such as glycolic acid, lactic acid, hydroxy acrylic acid, α-hydroxy butyric acid, glyceric acid, tartronic acid, maleic acid, tartaric acid, hydroxy benzoic acid, citric acid, salicylic acid, gallic acid, mandelic acid, tropic acid, ascorbic acid and gluconic acid; cinnamic acid, benzoic acid, phenylacetic acid, nicotinic acid, kainic acid, sorbic acid, pyrrolidone carboxylic acid, trimellitic acid, benzene sulfonic acid and toluene sulfonic acid; and acidic salts of these organic acids. Inorganic acids may also be used, including phosphoric acid, potassium dihydrogen phosphate, sodium dihydrogen phosphate, sodium sulfite, potassium sulfite, sodium pyrosulfite, potassium pyrosulfite, acidic sodium hexametaphosphate, acidic potassium hexametaphosphate, acidic sodium pyrophosphate, acid potassium pyrophosphate and sulfamic acid. Preferred examples of carbonate/acid combinations include sodium carbonate and/or sodium bicarbonate together with succinic and/or fumaric acid.

As detailed in U.S. patent application Ser. No. 07/324,885, when using fumaric acid, it is advantageous to incorporate either carboxymethyl cellulose (0.1–20%, by weight, based on fumaric acid content) or polyethylene glycol (0.2–20%, by weight, based on fumaric acid content) together with 0.02-0.1%, by weight, based on fumaric acid content of a nonionic surfactant having a hydrophile-lipophile balance of 7 or more.

These materials are combined with a powdered colloidal material, in tablet form. The colloidal material may include colloidal oatmeal, flours derived from corn, wheat, soy, rice, barley or other grains; cornmeal, almond meals and meals prepared from similar sources; hydrophobic or water-insoluble starch obtained from corn, wheat, rice, potato, or other grains, water-insoluble gums, cellulose, as well as mixtures of these materials. Colloidal oatmeal constitutes a preferred colloidal material for use in the claimed invention. Depending on the materials selected and the effect desired, the amount of colloidal material incorporated may vary from 0.1-50% (by weight), preferably 1-30% by weight, of the total composition of the tablet. With regard to colloidal oatmeal, documents submitted to the Food and Drug Administration by the manufacturer of AVEENO ® indicate that a final bath concentration of 0.007-10% colloidal oatmeal is sufficient to provide the intended benefit. Tablets may be formulated to provide this concentration in a single tablet, or using a plurality of tablets for each bath. If the formulation employs 20% colloidal oatmeal in a 50 gram tablet, the colloidal material obtained from one tablet will be present at a final concentration of 0.01%, assuming 25 gallons of water are present in the bath, providing 10 grams of colloidal oatmeal in 84.625 liters. It should be noted that at these types of concentrations, even if 40 gallons of water are used for the bath, the resulting concentration will be 0.007%, again, within the indicated guidelines.

As noted above, the preparation of carbonate salt/acid materials which dissolve to react and effervesce in warm or hot bath water is well known, and the composition thereof, per se, does not constitute an aspect of the invention of this application. However, generally, of the non-colloidal material present in the tablet of the invention, the organic acid is present in amounts of 10-350 wt. %, based on the carbonate salt present.

It is to be noted that it is necessary that the components of the bath preparation be in a physically bound form to secure all of the advantages described herein. Thus, agglomerated particles comprising the acid, carbonate and colloidal material, tablets made up of the same materials, prills, pills, capsules and the like may all be used in the practice of this invention. Tablets represent a preferred form. Not only is tablet form more convenient than current methods of delivering colloidal material to bath water, a simple mixture of raw materials added to bath water will result in rapid, uncontrolled gas generation without effective dispersion of the colloidal, particulate material. By using a tablet form, gas is generated in a controlled release to accelerate colloidal particles away and up from the bottom of the bath, improving dispersion. To this end, tableting/stabilizing materials may be used in the preparation of the tablet. Among these materials are polyethylene glycol, which, as noted above, also serves to suppress fumaric acid foaming. Crystalline sorbitol and magnesium oxide have also been demonstrated to be effective binder/stabilizer components. Other possible binders and stabilizers include sodium aluminate, microcrystalline cellulose, sodium alginate, polyvinyl alcohol, polyvinyl pyrrolidone, lactose, dextrin, dextrose monohydrate, starch, dibasic calcium phosphate dihydrate, sucrose, sugar, calcium sulfate dihydrate, carboxymethyl starch, polyacrylate copolymers and polymethacrylate. Reference is made to Lieberman et al, ed., *Pharmaceutical Dosage Forms: Tablets*, Volume 1, Chapter 2, "Tablet Formulation and Design", for further information regarding the preparation of stabilized tablets.

Other additives which may be included in amounts which will not interfere with effervescing activity or be irritating to the skin include perfumes, moisturizers, colorants, emollients, skin protectants, humectants, softening agents, sunscreens and the like. To improve tableting, flow improvers may be included in amounts of 0.1-5.0%, by weight, including such materials as calcium silicate, fumed silica, precipitated silica, hydrated silica, aluminum starch octenyl succinate, as well as other materials referred to in Lieberman, supra.

As detailed in U.S. patent application Ser. No. 07/331,207, filed Mar. 31, 1989, now pending, when using fumaric acid, sucrose stearate in limited amounts, e.g., 0.001-0.010%, by weight, may be added to reduce fumaric acid floating.

If the ratio of carbonate salt and acid is chosen so that the final product pH (0.01% solution) is weakly acid (pH 4-7), the benefits of carbon dioxide bathing, discussed in U.S. Pat. No. 4,666,707, along with the benefits of colloidal oatmeal, can be simultaneously obtained. At alkaline pH, carbon dioxide will be generated to disperse the colloidal particles, but will not remain dissolved in the water. Thus, under alkaline conditions, the invention herein can be used, but only the benefits of dispersion of colloidal materials will be apparent.

EXAMPLE

The dispersing effect of this invention can be illustrated by the following experiment. An example of the claimed invention was prepared by tableting a combination of sodium bicarbonate 18.460%, sodium carbonate 9.100%, succinic acid, 22.448% and fumaric acid, 9.638% and colloidal oatmeal, having a particle size meeting the definition proposed by S. C. Johnson to the FDA of less than 3% greater than 150 microns, and less than 20% greater than 75 microns, 20% by weight. Additionally, as binders and stabilizers polyethylene glycol (molecular weight 6000) was added in amount of 2.150%, crystalline sorbitol in an amount of 18.180% and magnesium oxide in amount of 0.20%. In light of the presence of fumaric acid, an additional 0.004% sucrose stearate was added, to complete the composition of the invention.

This example of the invention, as well as comparison examples, were placed in separate hot bath water (150 liters, 40° C). The water was stirred with a pole (ten revolutions, slow speed). After 4 minutes the water was passed through a sieve (250 micron openings). The residue was dried at 105° C. for 5 hours. The amount of material remaining is set forth below.

| Sample No. | Material | Grams Remaining |
| --- | --- | --- |
| 1 | Example of the Invention (10 g colloidal oatmeal) | 0.0 |
| 2 | Colloidal Oatmeal (10 g) | 2.0 |
| 3 | Colloidal Oatmeal (10 g) and Sodium Bicarbonate (9.3 g) | 0.7 |
| 4 | Colloidal Oatmeal (10 g) and Succinic Acid (11.9 g) | 1.4 |
| 5 | AVEENO ® (S. C. Johnson, 20 g) | 1.2 |

The invention disclosed above has been described both in general terms and by reference to specific components and examples. No limitations are intended or imposed by the exemplary materials, combinations and compositions recited, and alternatives will occur to those of ordinary skill in the art without the exercise of inventive faculty. In particular, carbonate, acid and colloidal material identities and weight relationships may be varied from the values set forth above, without departing from the scope of the invention, save as limited by the claims set forth below.

What is claimed is:

1. A bath preparation comprising:
   aggregated particles comprised of (1) a composition which will dissolve in warm and hot water to release carbon dioxide said composition comprising a carbonate salt and an acid, said composition (1) being intimately mixed with 0.1-50%, by weight, of a colloidal material suitable for treatment of skin, said colloidal material being selected from the group consisting of colloidal oatmeal, flour derived from corn, wheat, soy, rice or barley, meals obtained from corn or almond, hydrophobic starch obtained from corn, wheat, rice, potato, water-insoluble gums, cellulose and mixtures thereof.

2. The preparation of claim 1, wherein said mixture is in tablet form.

3. The mixture of claim 1, further comprising a stabilizer.

4. The mixture of claim 1, further comprising a flow improver.

5. The mixture of claim 1, wherein said acid is selected from the group consisting of fumaric acid, succinic acid and mixtures thereof.

6. The mixture of claim 5, wherein said mixture comprises fumaric acid.

7. The mixture of claim 6, wherein said composition (1) further comprises carboxymethyl cellulose 0.1-20%, by weight, based on fumaric acid content, polyethylene glycol 0.2-20%, by weight, based on fumaric acid content or mixtures thereof, together with an anionic surfactant with a hydrophile-lipophile balance of at least 7 and 0.2-0.1%, by weight, based on fumaric acid content.

8. The mixture of claim 7, wherein said composition (1) comprises sucrose stearate.

9. The mixture of claim 1, wherein said composition (1) is selected so as to provide bath water in which said tablet is dissolved with a pH of 4-7.

10. The mixture of claim 1, wherein said colloidal material is present in amounts of 0.5-30%, by weight.

11. The mixture of claim 1, wherein said acid is present in amounts of 10-350%, by weight, based on the amount of said carbonate.

12. The mixture of claim 1, further comprising at least one of perfumes, colorants, moisturizers, emollients, skin protectants, humectants, softening agents, sunscreens and topical medications.

13. A method of dispersing colloidal materials in water, comprising introducing the mixture of one of claims 1-4, 11 and 12 in water without substantial further agitation of said water, and allowing said composition (1') to effervesce.

14. A method of treating the skin, comprising introducing the mixture of any one of claims 1-4, 5, 10 and 11 to water, allowing said composition (1) to dissolve in said water and effervesce, and exposing said skin to the water in to which said mixture is introduced.

* * * * *